(12) United States Patent
Muller (10) Patent No.: US 6,712,759 B2
(45) Date of Patent: Mar. 30, 2004

(54) OUTFLOW SYSTEM FOR AN ENDOSCOPE (75) Inventor: Richard P. Muller, Bronx, NY (US)

(73) Assignee: ACMI Corporation, Southborough, MA (US)

( * ) Notice: Subject to any disclaimer, the term of this patent is extended or adjusted under 35 U.S.C. 154(b) by 29 days.

(21) Appl. No.: 10/041,645

(22) Filed: Jan. 7, 2002

(65) Prior Publication Data

US 2003/0130565 A1 Jul. 10, 2003

(51) Int. Cl.$^7$ ................................................ A61B 1/015
(52) U.S. Cl. ........................ 600/156; 600/129; 600/153
(58) Field of Search ................................ 600/156, 158, 600/153, 105, 130, 128, 129

(56) References Cited

U.S. PATENT DOCUMENTS

| | | | |
|---|---|---|---|
| 3,835,842 A | | 9/1974 | Igesias |
| 3,850,175 A | * | 11/1974 | Iglesias ...................... 600/156 |
| 4,132,227 A | * | 1/1979 | Ibe .............................. 600/129 |
| 4,920,961 A | | 5/1990 | Grossi et al. |
| 4,959,058 A | * | 9/1990 | Michelson .................. 600/156 |
| 5,320,091 A | * | 6/1994 | Grossi et al. ............... 600/156 |
| 5,392,765 A | | 2/1995 | Muller |
| 5,486,155 A | | 1/1996 | Muller et al. |
| 5,509,892 A | * | 4/1996 | Bonnet ........................ 600/156 |
| 5,549,541 A | | 8/1996 | Muller |
| 5,688,222 A | * | 11/1997 | Hluchy et al. .............. 600/156 |
| 5,807,240 A | * | 9/1998 | Muller et al. ............... 600/135 |
| 6,358,200 B1 | * | 3/2002 | Grossi ......................... 600/156 |
| 2002/0058859 A1 | * | 5/2002 | Brommersma .............. 600/156 |

OTHER PUBLICATIONS

Circon 1999–2000 Complete Product Catelog, (representative pages).

* cited by examiner

Primary Examiner—John P. Leubecker
(74) Attorney, Agent, or Firm—Ganz Law, PC; Bradley M. Ganz; James L. Wolfe (57) ABSTRACT

A sheath assembly for a medical instrument such as an endoscope comprises an outer sheath and inner sheath and novel means for providing out-flow of fluids from a surgical site. The outer sheath is disposed about at least a portion of an inner sheath. The assembly has an outflow aperture disposed in an outer wall at the distal end of the assembly. The outflow aperture is the initiation for an outflow conduit that is generally longitudinally disposed in a distal tip portion of the assembly and communicates fluid to a main outflow channel formed between the outer sheath and inner sheath. In a preferred embodiment, the outflow aperture and conduit are disposed wholly or partially in a dielectric tip element. The novel assembly allows improved outflow by disposing the outflow aperture at a more distal end of the instrument than conventional devices such that the outflow aperture is less prone to blockage by surrounding tissue or debris when used in tight anatomical passages.

38 Claims, 3 Drawing Sheets

OUTFLOW SYSTEM FOR AN ENDOSCOPE

BACKGROUND

1. Field of the Invention

The present invention relates generally to surgical devices for introduction into a patient in minimally invasive surgery. More particularly, the present invention relates to medical endoscopes and, even more particularly, to a continuous flow endoscope sheath assembly.

2. Background Art

Minimally invasive surgery reduces patients' surgery-induced trauma, pain, and infection risk. Minimally invasive surgery typically is performed through one or more portals, such as a body orifice or a small incision formed in the patient's body. The portals provide for introduction of surgical devices, such as endoscopes that allow viewing of the surgical site. The surgical instruments enable examination, therapeutic action, and operative actions. The therapeutic actions include, among other things, irrigating, suctioning, cutting, cauterizing, coagulating, vaporizing, retracting, stapling, and sampling tissue. The instruments may also provide operative actions such as distention of a body cavity, substance ingress, and substance egress.

By minimizing invasiveness, procedures are safer and atraumatic, patients recover more quickly, hospital stays are shortened, and health care costs may be decreased. Accordingly, minimizing invasiveness continues to be of importance, and there is a continuing need for devices and methods that achieve this objective.

One significant barrier to further minimization of invasiveness is that in many procedures, the instruments must have fluid inflow and outflow channels. These channels effectively add to the outer diameter of the instruments. For example, known endoscopic instruments provide inflow/outflow through an assembly of concentric sheaths that define channels for inflow and outflow of fluids to and from the operative or surgical site. For example, the fluid may be an irrigating solution that helps maintain a clear view of the site for the physician. Certain known irrigating systems provide continuous and simultaneous inflow and outflow. These systems are known as "continuous flow" systems.

The known continuous flow endoscope systems generally introduce an irrigating fluid into the surgical site from an external source. For this purpose, the endoscope has an inflow channel defined by the inner surface of the inner sheath. The fluid passes through the channel and exits the distal end of the sheath to irrigate the operative site. Fluid at the surgical site may be withdrawn through an outflow channel defined by the outer surface of the inner sheath and the inner surface of a surrounding outer sheath. The outflow channel initiates at the distal end (front end) of the instrument and transports fluid to an exit point at the proximal end of the outer sheath.

Examples of continuous flow systems include: U.S. Pat. Nos. 3,835,842; 5,392,765; 3,835,842; 4,920,961 (discloses a latching system for connecting inner and outer sheaths to each other and for connecting the inner sheath to a base element); 5,486,155 (discloses a rotatable continuous flow endoscope sheath); 5,320,091; and 5,392,765 (discloses a continuous flow cystoscope with a front top inlet). The foregoing patents are incorporated herein by reference in their entireties for all purposes, and more particularly to show certain devices that could be adapted to include the features of the present invention. (This incorporation by reference is not intended to be an admission that any referenced patent is prior art that would render claims appended hereto unpatentable.)

Figure 9:
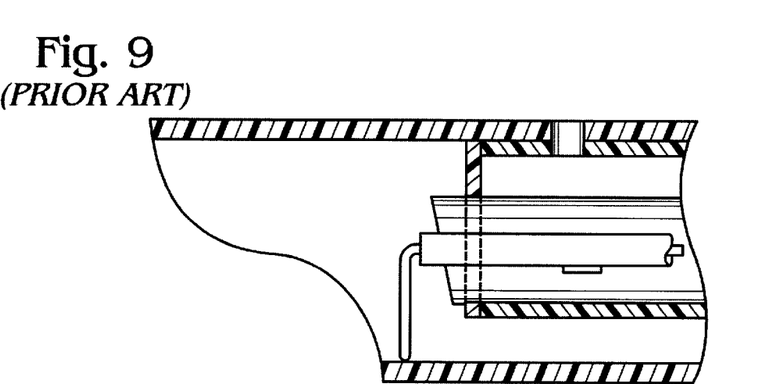
FIG. 9 is a side view cross section of an example of a prior art inner/outer sheath assembly for an endoscope.
Figure 10:
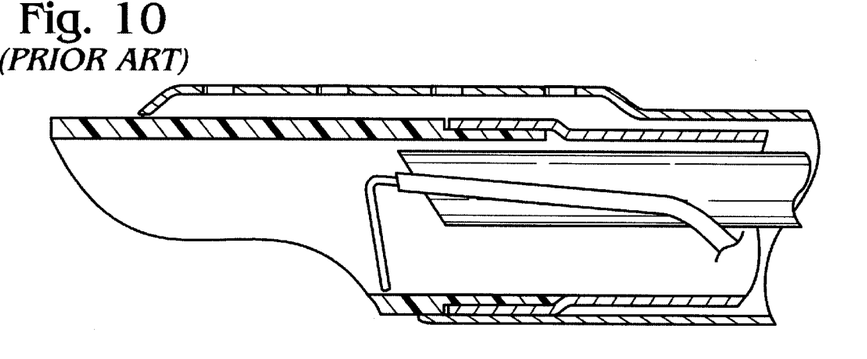
FIG. 10 is a side view cross section of an example of another prior art inner/outer sheath assembly for an endoscope.

Looking more particularly at the known devices, the outflow channel has a main distal aperture for withdrawing fluid. The aperture may be defined by the distal end points of the inner sheath or outer sheath (whichever has its distal end in a proximal position relative to the distal end of the other) and the points on the inner or outer sheath that are on common perpendicular lines off the longitudinal axis of the outflow channel. In other words, if the inner sheath is recessed within the outer sheath, and all points on the distal end of the inner sheath lie in a single plane transverse to the longitudinal axis of the inner sheath, then the aperture for the outflow channel is defined by the transverse plane through the inner sheath and extending through the surrounding outer sheath. This is the case, for example, in U.S. Pat. No. 3,835,842, where the distal end of the outer sheath extends distally beyond the distal end of the inner sheath (represented in FIG. 9). In other cases, as seen in U.S. Pat. No. 4,132,227 (represented in FIG. 10), the distal end of the inner sheath extends distally beyond the distal end of the outer sheath. The points on the distal end of the outer sheath do not lie in a single plane. Therefore, the outflow aperture does not have points that lie in a single transverse plane, i.e., the aperture initiates at a distal location and terminates at a proximal location. A significant drawback of this arrangement is that the aperture, which generally has an annular profile because it is defined by the space between sheaths, has a limited area for outflow. Increasing the space between sheaths to increase the outflow area would necessitate a corresponding increase in the outer diameter of the sheath assembly. This, of course, runs contrary to the objective of minimizing invasiveness.

There has been some effort to address the foregoing problem, but it has not been adequate. In known devices, in addition to a main outflow aperture at the front end of the device, the outer surface of the outer sheath has one or more lateral outflow apertures for passing fluid from the exterior of the outer sheath into the outflow channel. It is significant that in the known devices, these secondary outflow apertures on the outer sheath are disposed proximal (behind) the inflow aperture at the distal (front) end of the inner sheath. This is largely because the outflow holes would necessarily be positioned sufficiently proximal from the distal structure of the inner sheath so as to provide for unimpeded outflow through the holes and into the outflow channel between inner and outer sheaths. As a consequence, these lateral outflow holes generally lie well proximal to the inflow aperture. Unfortunately, there are inherent, unresolved disadvantages in tip portions having outflow apertures disposed proximal to the inflow aperture. For example, tissue or debris at the surgical site may press against the lateral outflow apertures, blocking them. This reduces outflow capacity.

In endoscopes such as resectoscopes, which are used with electrosurgical throughput devices, such as cutting, coagulating, or vaporizing electrodes, the distal tip portion of the inner or outer sheath assembly includes a dielectrical tip. The dielectrical tip insulates the electrode element from the outer and inner sheaths, which are generally made of electrically conductive metal. In general, the tip is a tube-like extension of the outer or inner sheath. However, the tip may take other configurations, such as a partial tube, beak, shield, etc. In the known devices, the insulative tip does not provide lateral apertures for outflow. Therefore, lateral outflow apertures in the known devices are situated even further behind the inflow aperture, and provide inadequate outflow at the distal tip portion of the endoscope. This is particularly disadvantageous where such instruments are used in tight anatomical spaces.

Another disadvantage of having a dielectrical tip placed on the end of the inner sheath is that common dielectrical materials are brittle and prone to fracturing when the inner sheath is physically withdrawn from the outer sheath.

For at least the foregoing reasons, there is a significant need for improved outflow systems in endoscopes and other invasive medical instruments requiring outflow functions, and particularly in endoscopes used with electrosurgical throughput devices where dielectrical tips must be used.

SUMMARY OF THE INVENTION

The present invention overcomes the aforementioned disadvantages by providing an improved outflow mechanism in a tip portion in an assembly of an inner and outer sheath. One significant advantage of the present invention is its improved mechanism for outflow in tight anatomical passages. In certain embodiments, another significant advantage is that, without compromising outflow efficiency, the dielectrical tip may be placed on the outflow sheath where it is much less prone to damage or fracture from the assembly and disassembly of the inner sheath from outer sheath. Placement of the dielectrical tip on the outer sheath also allows for a heavier wall thickness of the distal aperture of the sheath thereby affording a less sharp and traumatic entry through the patient's orifice and tissue.

More particularly, in one possible embodiment the present invention is directed to an assembly of sheaths for use in a medical instrument such as an endoscope. The assembly includes an outer sheath and inner sheath for providing inflow and outflow of fluids at a surgical site. In the assembly, an outer sheath is disposed about at least a portion of an inner sheath, and an outflow channel is disposed between the inner sheath and the outer sheath. The assembly further includes an outflow conduit with an outflow aperture initiating in an outer wall at the distal end of the assembly. The outflow conduit is disposed generally in a longitudinal direction and communicates with the more proximal outflow channel formed between the outer sheath and inner sheath so that fluid may be directed from the outflow conduit into the outflow channel.

In the foregoing assembly, the outflow conduit may initiate in a distal tip portion of the sheath in a position distal to a main inflow hole for the inner sheath assembly. In the assembly, the outflow aperture may initiate in a distal tip portion of a lateral surface of the outer sheath and merge into the outflow channel at a position proximal to the inflow hole. The inflow hole may comprise an opening at the distal end of the inner sheath. In the assembly, the outer sheath may comprise a tube and a dielectrical tip element, the tip element being affixed to the distal end of the tube. In the assembly, the tip element may have a distal portion that extends distally from within the outer tube and a proximal portion affixed to an inner surface of the outer tube, the outflow conduit being defined at least in part by a space between the proximal portion of the tip element and an inner surface of the outer tube. In the assembly, there may be a plurality of outflow conduits disposed circumferentially about the distal tip of the assembly in a position proximal to the inflow hole. In the assembly, there may be one or more thru-holes disposed in the outer surface of the assembly distal to the inflow hole at the distal end of the inner sheath. In the assembly, the tip element may comprise a ceramic material.

In another possible embodiment, the present invention is directed to a medical endoscope having an outer sheath surrounding at least a portion of an inner sheath and an outflow channel disposed therebetween. The inner sheath has an inflow hole at its distal end in an inflow channel; the outer sheath has a distal tip portion. At least one outflow conduit is disposed in an outer surface of the tip portion, the outflow conduit communicating with the outflow channel. The conduit initiates with an inflow aperture disposed on the surface of the distal tip portion at a position distal to the inflow hole at the inner sheath.

In the foregoing endoscope, the distal tip portion may include a section comprising a dielectrical material. In the endoscope, the section of the tip portion may comprise a dielectrical tip element affixed to the distal end of the inner or outer sheath. The endoscope may further include a working element. The working element may hold the outer and inner sheaths in a position such that the distal end of the inner sheath is proximal the outflow conduit. The working element may include means for communicating fluid to the inflow hole through an inflow channel in the inner sheath. The working element may include a channel for inserting a throughput device through an opening at the proximal end of the instrument. The channel may comprise the inflow channel of the inner sheath. The endoscope of the foregoing embodiment may include a telescope, electrode, and/or other throughput devices as components of the assembly. In one possible variation, the endoscope is a resectoscope.

In another possible embodiment, the present invention is directed to a method of constructing a medical endoscope. The method is carried out by providing an inner sheath and outer sheath and assembling the two such that for at least a portion of the inner sheath, an outflow channel is disposed between the inner sheath and outer sheath, the assembly having an outflow conduit with an outflow aperture initiating in an outer wall at the distal end of the assembly, the conduit being disposed generally in a longitudinal direction and communicating with the outflow channel formed between the outer sheath and inner sheath so that fluid may be directed from the outflow conduit into the outflow channel.

In the foregoing method, the outflow conduit may initiate in a distal tip portion of the sheath in a position distal to a main inflow hole for the sheath assembly. In the method, the outflow aperture may initiate in a distal tip portion of a lateral surface of the outer sheath and merges into the outflow channel at a position proximal to the inflow hole. In the method, the inflow hole may include an opening at the distal end of the inner sheath. In the method, the outer sheath may include a tube and a dielectrical tip, the tip element being affixed to the distal end of the tube. In the method, the tip element may have a distal portion that extends distally from within the outer tube and a proximal portion affixed to an inner surface of the outer tube, the outflow conduit being defined at least in part by a space between the proximal portion of the tip element and an inner surface of the outer tube. In the method, there may be a plurality of outflow conduits disposed circumferentially about the distal tip of the assembly in a position proximal to the inflow hole. In the method, one or more thru-holes may be disposed in the outer surface of the assembly distal to the inflow hole at the distal end of the inner sheath. In the method, the tip element may comprise a ceramic material.

In another possible embodiment, the present invention is directed to a method of using a medical instrument in a surgical procedure. The method provides for inserting into a surgical site of a patient an assembly of an outer sheath and inner sheath for providing inflow and outflow of fluids at a surgical site. In the assembly, the outer sheath is disposed about at least a portion of the inner sheath, and an outflow channel is disposed between the inner sheath and outer sheath. The assembly has an outflow conduit with an outflow aperture initiating in an outer wall at the distal end of the assembly. The outflow conduit is disposed generally in a longitudinal direction and communicating with the outflow channel formed between the outer sheath and inner sheath so that fluid may be directed into the outflow channel from the outflow conduit. The outflow conduit initiates in a distal tip portion of the sheath in a position distal to a main inflow hole for the sheath assembly withdrawing fluid through the outflow channel via the outflow conduit and associated outflow aperture.

In the foregoing method, the conduit may initiate in a distal tip portion of the sheath in a position distal to a main inflow hole for the sheath assembly. In the method, the outflow aperture may initiate in a distal tip portion of a lateral surface of the outer sheath and merges into the outflow channel at a position proximal to the inflow hole. In the method, the inflow hole may comprise an opening at the distal end of the inner sheath. In the method, the outer sheath may comprise a tube and a dielectrical tip element, the tip element being affixed to the distal end of the tube. In the method, the tip element may have a distal portion that extends distally from within the outer tube and a proximal portion affixed to an inner surface of the outer tube, the outflow conduit being defined at least in part by a space between the proximal portion of the tip element and an inner surface of the outer tube. In the method, one or more thru-holes may be disposed in the outer surface of the assembly distal to the inflow hole at the distal end of the inner sheath. The medical instrument may be used in medical procedures, such as transurethral resection of the prostate, transurethral resection of a bladder tumor, or hysteroscopic endometrial ablation, the procedures being well know to persons skilled in the art.

In another possible embodiment, the present invention is directed to a tip element adapted to be affixed to the distal end of an inner sheath or outer sheath of a medical endoscope, the tip element having a plurality of outflow openings disposed laterally in the outer surface of the element, the openings including sidewalls and in combination with a surface of the outer sheath or inner sheath defining outflow conduits for communicating longitudinally with an outflow channel of a sheath assembly in the endoscope.

The foregoing tip element may comprise a dielectrical material, such as ceramic. In the foregoing tip element, the openings have a distal portion for providing outflow apertures for an assembly of inner and outer sheaths in an endoscope.

In another possible embodiment, the present inventions is directed to a medical endoscope having an electrically conductive outer sheath, an electrically conductive inner sheath, and a working element. The outer sheath surrounds the inner sheath and defines an outflow channel, and the inner sheath defines an inflow channel. The outer sheath has a distal tip portion, wherein the tip portion is made substantially of a dielectrical composition and is disposed at the distal end of the outer sheath. The tip element has a plurality of outflow openings, the openings including sidewalls and, in combination with a surface of the outer sheath or inner sheath, defining an outflow conduit. In the assembly, the working element holds the outer sheath and inner sheath in a position such that the distal end of the inner sheath is proximal to the inflow apertures for the outflow conduits and the outflow conduits merge with an outflow channel at a position proximal the inflow hole at the distal end of the inner sheath. The working element includes a portal for receiving an active cord for a throughput device.

In the foregoing endoscope, the tip element may comprise a ceramic tip. In the foregoing endoscope, a portion of the outer sheath proximal the inflow at the distal end of the inner sheath may contain a plurality of outflow holes directly communicating with the outflow channel. In the endoscope, the working element may hold the outer sheath and inner sheath in a position such that the distal end of the inner sheath is proximal to the inflow apertures for the outflow conduits and the outflow conduits merge with an outflow channel at a position proximal the inflow hole at the distal end of the inner sheath In another possible embodiment, the present invention is directed to a continuous flow endoscope, such as a resectoscope, used with an electrosurgical throughput device. The endoscope has a dielectrical or insulated tip portion attached to an outer sheath. The insulated sheath tip has a plurality of axial grooves circumferentially spaced about at least a portion of its outside surface such that irrigant outflow can occur from the very distal end of the outer sheath, through openings at the juncture of the insulated tip and the outer sheath tube, and then through the outflow channel between the inner and outer sheaths of the continuous flow sheath assembly, and then out of the device.

Many of the various features of novelty that characterize the invention are pointed out with particularity in the claims annexed to and forming a part of this specification. For a better understanding of the invention, its operating advantages and specific objectives attained by its use, reference should be made to the accompanying drawings and descriptive matter in which its preferred embodiments are illustrated and described. In drawings, like reference numerals identify the same or similar elements.

DETAILED DESCRIPTION

To illustrate the principles of the present invention, this specification will discuss the present invention in terms of a continuous flow endoscope system. It is particularly directed to a resectoscope system for use with an electrosurgical throughput device. Such devices include known electrodes for cutting, coagulating, cauterizing, or vaporizing tissue. Although the present invention will be described with reference to the embodiments shown in the drawings, features of the present invention can be embodied in various different embodiments and alternative types of endoscopes. In addition, any suitable size, shape or type of elements or materials could be used.

Referring to FIGS. 1–8, a resectoscope 10 generally comprises a working element 12, an assembly of inner and outer sheaths 16, and a removable telescope 14. A throughput device 18 may be inserted through the sheath assembly. The throughput device may be any device that interacts with the surgical site into which the distal end of the resectoscope is placed. For example, the throughput device may be a tool, such as an electrode or a fiber optic laser guide.

Figures 1, 2, 3:
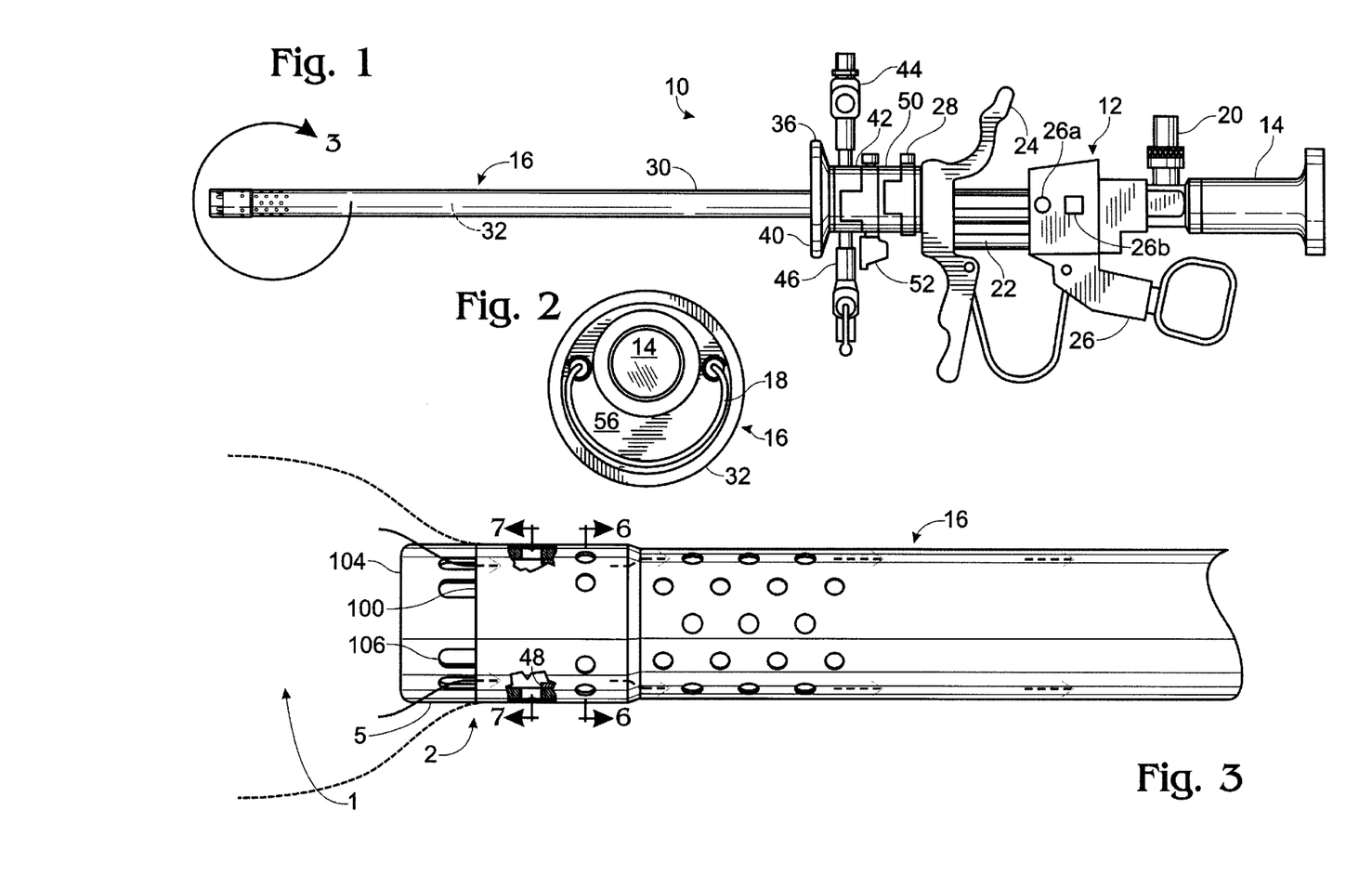
FIG. 1 is an elevational side view of an endoscope incorporating features of the present invention.
FIG. 2 is a distal (front) elevational view of the endoscope shown in FIG. 1.
FIG. 3 is an enlarged elevational side view of a distal portion of the endoscope shown in FIG. 1.

The working element 12 and telescope 14, in the embodiment shown, are generally representative of a U.S.A. ELITE SYSTEM working element and telescope available from Circon Corporation of Stamford, Conn. The telescope 14 is removably mounted to the working element 12, and has a connector 20 for connecting fiber optics in the telescope with a light source by means of a flexible light transmitting cable (not shown). The working element 12 generally comprises a frame 22, a front handle 24, a movable portion 26, and a latch assembly 28. The working element 12, telescope 14 and throughput devices are well known in the art. In alternative embodiments, any suitable type of working element, telescope and/or throughput device could be used.

The moveable portion 26 generally incorporates an electrode locking mechanism 26a and a portal 26b for attaching an active cord from the electrosurgical generator to the electrode proximal end (not shown).

The sheath assembly 16 generally comprises an outer sheath 30 and an inner sheath 32. The outer sheath 30 generally comprises outer tube 34. It may include rear end section 36. The outer tube 34 preferably has a circular cross-section, but other cross sections are possible. For example, it could have a generally oval shape or any other suitable shape for holding the inner sheath 32 or forming inflow or outflow channels. The sheath assembly 16 has a distal tip portion 104 (discussed in more detail below). The outer sheath is shown with lateral holes 38 in its front end. The rear end section 36 is attached to the rear of the outer tube 34. The rear end section 36 has a shield 40, a connector 42, a fluid inlet 44 and a fluid outlet 46.

The inner sheath 32 generally comprises inner tube 48, and may include a frame member 50 and a movable latch 52. The inner tube is concentrically disposed within outer tube 34. The inner surface of the inner sheath defines an inflow channel 68 having a main inflow hole 56. The distal end of the inner tube 48 is a predetermined distance within the outer tube 34 but forward of lateral outflow apertures 38 in the outer tube.

The inflow channel 68 forms a path for fluid to pass from the fluid inlet 44 and frame member 50 to the inflow hole 56 in tip portion 104. The inflow channel may also simultaneously accommodate telescope 14 and device 18. (Telescope 14 and device 18 are omitted from FIG. 5).

For improved outflow at a surgical site 1, the present invention provides a novel design for the distal tip portion 104 of an assembly of outer and inner sheaths. In this respect, the present invention provides one or more novel outflow conduits 100 that are capable of extending into the cavity or area of a surgical site so that they are less likely to be blocked by a tight passage 2 of tissue leading into the site or from debris at the site. In the present invention, one or more outflow apertures 102 are disposed in the outer, lateral surface of the assembly so outflow initiates at a more distal position along the lateral side of the instrument than afforded by the prior devices. Looking at FIG. 5, in sheath assembly 16 each aperture 102 initiates in the outer surface of the sheath assembly at a position 106 distal to inflow hole 56 at the distal end of inner sheath 32. (The initiation point 106 shown in the drawings is just an example position; the aperture 102 may initiate anywhere along a line from the distal end of sheath 32 to the inflow hole.) The aperture 102 continues as an outflow conduit 100 communicating with the outflow channel 70 formed between the outer sheath 30 and inner sheath 32 so that fluid may be directed into the outflow channel 70. Accordingly, the outflow conduit extends generally longitudinally within sheath assembly 16 from its initiation point at outflow aperture 102 in the surface of the sheath assembly. The outflow conduit 100 carries fluid proximally beyond the distal end of inner sheath 30 before merging with the outflow channel 70 at position 108. Position 108 preferably is proximally beyond the main inflow aperture 56 to minimize conflict between the fluid dynamics of inflow and outflow.

In one possible embodiment, each outflow conduit 100 initiates with an outflow aperture 102 disposed in the outer wall or surface of distal tip portion 104 of outer sheath 30. Each outflow aperture 102 is oriented on a lateral side surface of the outer sheath generally perpendicular to the plane of main inflow hole 56 at the distal end of the sheath assembly 16. The outflow channel 70 is the space between the concentric sheaths 30 and 32. However, the outer sheath 30 need not completely surround the inner sheath 32 to form a channel capable of transporting fluids away from the surgical site. For example, the channel 70 could be defined as any geometrical cross-sectional shape of the inner sheath, so long as a fluid flow path is defined. For further example, outflow channel 70 could be defined in an elongate unitary or integral piece of material with a longitudinal partition, creating one or more separate channels for outflow and/or devices. The channels, for example, could run, coaxially, in parallel or otherwise generally longitudinally. The apertures 102 are preferably spaced about the circumference of the outer sheath to provide fluid egress from all positions in a surgical site. The positioning and spacing may be adjusted to suit particular needs. While channel 70 between the outer sheath and inner sheath may be extended to the distal tip of assembly 16 to provide outflow from the surgical site, the laterally positioned outflow apertures 102 and conduits 100 do not substantially increase the outer diameter of the assembly, which would go against principles of minimally invasive surgery. The lateral positioning means that fluid egress needs may be addressed by increasing the total open area in the lateral surface of sheath assembly 16 without significantly adding to the outer diameter of the assembly. The apertures 102 may take any suitable shape or size. As indicated in the figures, a suitable shape is an elongate hole stretching longitudinally along and through the surface of the outer sheath 30.

The novel arrangement of an outflow aperture and conduit overcomes the limitations in the prior art where the lateral outflow apertures are disposed proximal the main inflow aperture. The novel features permit fluid outflow from a position closer to the distal end of the sheath assembly and in front of a main inflow aperture (e.g. inflow hole 56) while maintaining the full aperture of the inner sheath diameter available for the telescope, devices, and inflow of fluid. So-positioned apertures deliver fluid via conduits 100 to a main outflow channel at a position proximal to the main inflow aperture. This outflow system helps avoid conflicting fluid dynamics, while initiating fluid outflow at a position less likely to be impeded by anatomy.

In addition to the novel arrangement of outflow conduits 100, the sheath assembly may also carry conventional outflow holes 38 in a conventional position proximal to the inflow hole 56 at the distal end of sheath 32. As discussed earlier, in endoscopes used with electrosurgical throughput devices, such as cutting, coagulating, or vaporizing electrodes, the distal tip of the inner or outer sheath assembly may include a dielectric tip portion for electrically insulating the electrode element from the outer and inner sheaths. In general, the dielectrical portion may be a tube-like extension of the outer or inner sheath.

For example, in the embodiment shown, outer sheath 30 comprises outer tube 34 and insulative tip element 5 disposed on the distal end of the outer tube 34. The tip element 5 may be removably or permanently attached or otherwise integrated into the distal end of sheath assembly 16. It may comprise tip portion 104 in whole or part. The tip 5 is preferably made of a dielectrical material, such as ceramic or a molded plastic or polymer material. The dielectrical tip portion 5 may also take the form of an insulating coating or laminate on the inner and/or outer surfaces of one or both tubes comprising tip portion 104. The dielectrical tip portion is a design option. For example, in other possible embodiments, such as when the device 18 is a laser, the tip 5 could be comprised of metal and be an integral feature of the inner sheath tube, not a separate part. In addition to what is shown in the figures, dielectric tip portion 5 may take various configurations, such as a partial tube, beak, shield, or any other tip configuration desired tip portion 104.

The dielectric tip element 5 if present, forms the distal end of the sheath assembly 16. In the prior art, this dielectrical tip element 5 does not provide lateral apertures and/or channels for outflow. Therefore, outflow apertures in prior electrosurgical endoscopic devices are not optimally disposed at the distal end of the assembly of the inner and outer sheaths. Accordingly, the present invention overcomes the inherent disadvantages of such devices by incorporating lateral apertures 102 and conduits 100 in whole or part in tip element 5 in a tip portion 104.

Figure 4:
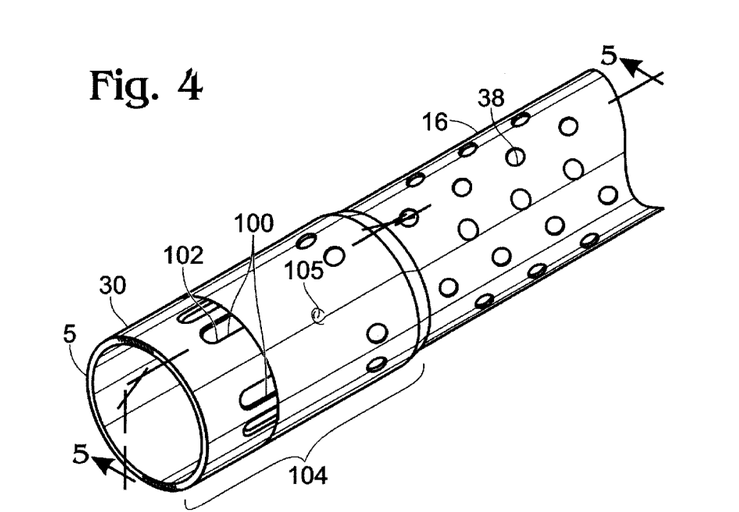
FIG. 4 is an enlarged perspective view of a distal portion of the endoscope shown in FIG. 3.
Figure 7:
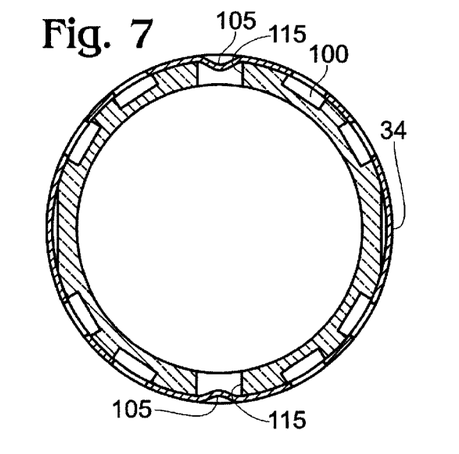
FIG. 7 is a cross-sectional view of the distal portion of the endoscope shown in FIG. 3, taken along line 7—7.
Figure 8:
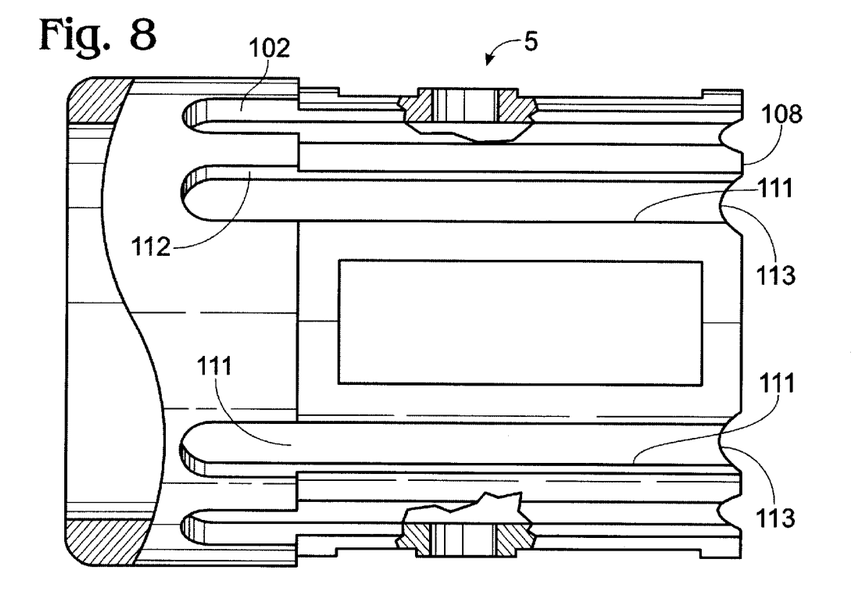
FIG. 8 is a partial cross-sectional side view of a distal tip extension for use in a distal portion of an endoscope such as that of FIGS. 1–7.

FIG. 8 illustrates features of one possible tip element 5 with outflow apertures 102. The tip may be formed of ceramic, or any other suitable dielectric material, as noted above. In the embodiment of FIG. 8, the tip element 5 is a hollow, generally cylindrically shaped element. Tip element 5 has a plurality of elongate openings 110 disposed in its outer surface for use as outflow apertures 102 and in forming outflow conduits 100. The openings 110 extend longitudinally along arcuate side wall 111 of the element. The openings also have vertical side wall 112 perpendicularly oriented relative to side wall 111. The tip element 5 may be affixed to the sheath assembly 16 by conventional means such as chemical bonding (e.g., epoxy) or mechanical fastening (e.g., swaged or pinned). In a preferred embodiment, tip element 5 is a complementary size and shape for a close fit within the distal end of sheath 30. As an example, FIGS. 4 and 7 show a mechanical retention means 105 disposed on the outer sheath 30 that mates with an opening or recess, such as thru-hole 115, in tip 5 to help secure the tip and sheath 30 together. This retention means could be used in conjunction with the adhesive to maintain the attachment of the tip and sheath in case the adhesive failed. In the example shown, the retention means comprises a dimpled-in area of tubing.

Figure 5:
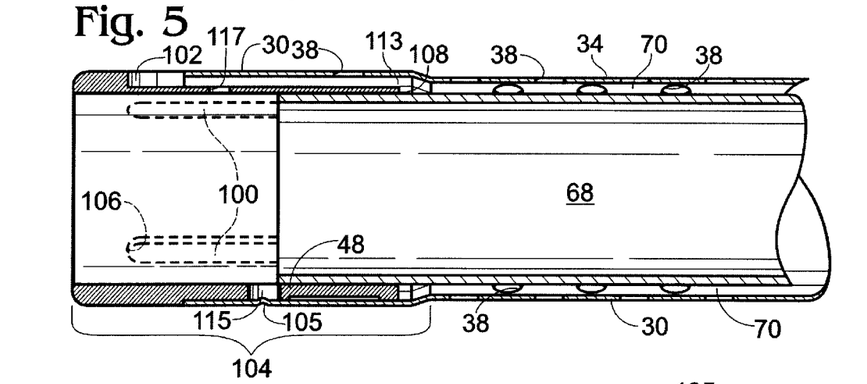
FIG. 5 is a cross-sectional view of the distal portion of the endoscope shown in FIG. 4, taken along line 5—5, showing one possible arrangement of distal tip, inner sheath, and outer sheath, in accordance with the present invention.
Figure 6:
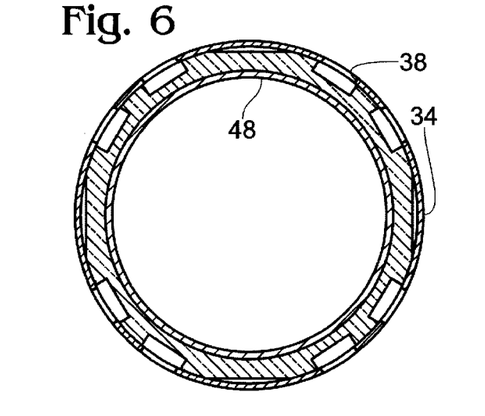
FIG. 6 is a cross-sectional view of the distal portion of the endoscope shown in FIG. 3, taken along line 6—6.

As indicated in FIGS. 4 and 5, the distal end of the outer sheath at tip portion 104 may be slightly larger in diameter than the proximal portion to receive the diameter of tip element 5. The proximal portion of the element 5 is sufficiently recessed within sheath 30 that the sheath covers a proximal portion of the openings 110. The exposed portions of the openings 110 comprise outflow apertures 102 (bounded by arcuate side wall 111). The covered portions, in combination with the inner surface of sheath 30, define outflow conduits 100. As indicated in figures, there is a reduced or no vertical side wall 112 at the proximal end of openings 110 so that there is a more open end 113 for fluid to flow into the proximally adjacent outflow channel 70. The size, shape and positioning of the openings 110 may be varied to provide the scope of outflow apertures and conduits contemplated by the other descriptions of each elsewhere herein.

As seen in FIG. 5, the present invention may optionally include one or more optional thru-holes 115 disposed in the inner surface of tip 5 and communicating with the outflow conduit at a position just distal a main inflow hole 56. The thru-holes 115 help remove gas bubbles that may collect at the inflow hole 56. Removal of bubbles helps ensure proper flow conditions and obstructed vision through the telescope. Any bubbles pass through a hole 115 into outflow conduit 100.

Persons skilled in the art will recognize the foregoing description and embodiments are not limitations, but examples. It will be recognized by persons skilled in the art that many modifications and variations are possible in the details, materials, and arrangements of the parts and steps which have been described and illustrated in order to explain the nature of this invention, and that such modifications and variations do not depart from the spirit and scope of the teachings and claims contained herein.

What I claim:

1. An assembly of an outer sheath and inner sheath for providing inflow and outflow of fluids at a surgical site comprising: an outer sheath disposed about at least a portion of an inner sheath, and an outflow channel disposed between the inner sheath and outer sheath, the assembly having an outflow conduit with an outflow aperture initiating in an outer wall at the distal end of the assembly, the conduit being disposed generally in a longitudinal direction and communicating with the more proximal outflow channel formed between the outer sheath so that fluid may be directed from the outflow conduit into the outflow channel;

wherein the outflow conduit initiates in a distal tip portion of the sheath assembly in a position distal to a main inflow hole for the sheath assembly; and wherein the tip portion comprises a dielectrical tip element disposed at the distal end of the outer sheath, the tip element having a plurality of lateral outflow openings, the openings being in fluid communicating with a channel between the inner and outer sheaths.

2. The assembly of claim 1 wherein the outflow aperture initiates in a distal tip portion of a lateral surface of the outer sheath and merges into the outflow channel at a position proximal to the inflow hole.

3. The assembly of claim 2 wherein the inflow hole comprises an opening at the distal end of the inner sheath.

4. The assembly of claim 2 wherein the outer sheath comprises a tube and a dielectrical tip element, the tip element being affixed to the distal end of the tube.

5. The assembly of claim 4 wherein the tip element has a distal portion that extends distally from within the outer sheath and a proximal portion affixed to an inner surface of the outer tube, the outflow conduit being defined at least in part by a space between the proximal portion of the tip element and an inner surface of the outer tube.

6. The assembly of claim 5 wherein the tip element comprises a ceramic material.

7. The assembly of claim 2 wherein there is a plurality of the outflow conduits disposed circumferentially about distal tip of the assembly.

8. The assembly of claim 2 wherein one or more thru-holes are disposed in the outer surface of the assembly distal to the inflow hole at the distal end of the inner sheath.

9. A medical endoscope comprising an outer sheath and inner sheath and a working element: the outer sheath surrounding at least a portion of the inner sheath and defining an outflow channel, the inner sheath defining an inflow channel; and the outer sheath having a distal tip portion, wherein the tip portion comprises a dielectrical tip element disposed at the distal end of the outer sheath, the tip element having a plurality of lateral outflow openings, the openings being in fluid communicating with a channel between the inner and outer sheaths.

10. The endoscope of claim 9 wherein the working element holds the outer sheath and inner sheath in a position such that the distal end of the inner sheath is proximal to the inflow apertures for the outflow conduits and the outflow conduits merge with an outflow channel at a position proximal the inflow hole at the distal end of the inner sheath.

11. The endoscope of claim 10 wherein the tip elements comprises a ceramic tip.

12. The endoscope of claim 10 wherein a portion of the outer sheath proximal the inflow at the distal end of the inner sheath contains a plurality of outflow holes directly communicating with the outflow channel.

13. The endoscope of claim 12 further comprising a thru-hole disposed in the tip element at a position distal the inflow hole and the hole communicating directly with an outflow conduit.

14. A method of constructing a medical instrument comprising: providing an inner sheath and outer sheath and assembling the two such that for at least a portion of an inner sheath, an outflow channel is disposed between the inner sheath and outer sheath, the assembly having an outflow conduit with an outflow aperture initiating in an outer wall at the distal end of the assembly, the conduit being disposed generally in a longitudinal direction and communicating with the outflow channel formed between the outer sheath and inner sheath so that fluid may be directed from the outflow conduit into the outflow channel;
   wherein the outflow conduit initiates in a distal tip portion of the sheath assembly in a position distal to a main inflow hole for the sheath assembly; and
   wherein the tip portion comprises a dielectrical tip element disposed at the distal end of the outer sheath, the tip element having a plurality of lateral outflow openings, the openings being in fluid communication with a channel between the inner and outer sheaths.

15. The method of claim 14 wherein the outflow conduit initiates in a distal tip portion of the sheath in a position distal to a main inflow hole for the sheath assembly.

16. The method of claim 15 wherein the outflow aperture initiates in a distal tip portion of a lateral surface of the outer sheath and merges into the outflow channel at a position proximal to the inflow hole.

17. The method of claim 16 wherein the inflow hole comprises an opening at the distal end of the inner sheath.

18. The method of claim 17 wherein one or more thru-holes are disposed in the outer surface of the assembly distal to the inflow hole at the distal end of the inner sheath.

19. The method of claim 16 wherein the outer sheath comprises a tube and a dielectrical tip element, the tip element being affixed to the distal end of the tube.

20. The method of claim 19 wherein the tip element has a distal portion that extends distally from within the outer tube and a proximal portion affixed to an inner surface of the outer tube, the outflow conduit being defined at least in part by a space between the proximal portion of the tip element and an inner surface of the outer tube.

21. The method of claim 19 wherein the tip element comprises a ceramic material.

22. The method of claim 16 wherein there is a plurality of outflow conduits disposed circumferentially about the distal tip of the assembly in a position proximal to the inflow hole.

23. A method of using a medical instrument in a surgical procedure comprising, inserting into a surgical site of a patient an assembly of an outer sheath and inner sheath for providing inflow and outflow of fluids at a surgical site, the outer sheath is disposed about at least a portion of the inner sheath, and an outflow channel is disposed between the inner sheath and outer sheath, the assembly having an outflow conduit with an outflow aperture initiating in an outer wall at the distal end of the assembly, the conduit is disposed generally in a longitudinal direction and communicates with the outflow channel formed between the outer sheath and inner sheath so that fluid may be directed into the outflow channel from the outflow conduit; and, withdrawing fluid through the outflow channel via the outflow conduit and associated outflow aperture;
   wherein the outflow conduit initiates in a distal tip portion of the sheath assembly in a position distal to a main inflow hole for the sheath assembly; and
   wherein the tip portion comprises a dielectrical tip element disposed at the distal end of the outer sheath, the tip element having a plurality of lateral outflow openings, the openings being in fluid communicating with a channel between the inner and outer sheaths.

24. The method of claim 23 wherein the conduit initiates in a distal tip portion of the assembly sheath in a position distal to a main inflow hole for the sheath assembly.

25. The method of claim 24 wherein the outflow aperture initiates in a distal tip portion of a lateral surface of the outer sheath and merges into the outflow channel at a position proximal to the inflow hole.

26. The method of claim 25 wherein the inflow hole comprises an opening at the distal end of the inner sheath.

27. The method of claim 25 wherein the outer sheath comprises a tube and a dielectrical tip element, the tip element being affixed to the distal end of the tube.

28. The method of claim 27 wherein the tip element has a distal portion that extends distally from within the outer tube and a proximal portion affixed to an inner surface of the outer tube, the outflow conduit being defined at least in part by a space between the proximal portion of the tip element and an inner surface of the outer tube.

29. The method of claim 26 wherein one or more thru-holes are disposed in the outer surface of the assembly distal to the inflow hole at the distal end of the inner sheath.

30. The method of claim 23 wherein the assembly is used in a medical procedure comprising transurethral resection of the prostate, transurethral resection of a bladder tumor, or hysteroscopic endometrial ablation.

31. A dielectrical tip element adapted to be affixed to the distal end of an inner sheath or outer sheath of a medical endoscope, the tip element having a plurality of outflow openings disposed laterally in the outer surface of the element, the openings including sidewalls, the tip element being combinable with a surface of the outer sheath or inner sheath to define at least one outflow conduits for communication longitudinally with an outflow channel of a sheath assembly in the endoscope; and wherein the at least one outflow conduit initiates in a distal tip portion of the sheath assembly in a position distal to a main inflow hole for the sheath assembly.

32. The tip element of claim 31 wherein the element comprises a dielectrical material.

33. The tip element of claim 32 wherein the tip element comprises a ceramic material.

34. The tip element of claim 32 wherein the openings have a distal portion for providing outflow apertures for an assembly of inner and outer sheaths in an endoscope.

35. A medical endoscope comprising an electrical conductive outer sheath, an electrically conductive inner sheath, and a working element; the outer sheath surrounding the inner sheath and defining an outflow channel, the inner sheath defining an inflow channel; and the outer sheath having a distal tip portion, wherein the tip portion comprises a dielectrical tip element disposed at the distal end of the outer sheath, the tip element having a plurality of outflow openings, the openings including sidewalls and, in combination with a surface of the outer sheath or inner sheath, defining an outflow conduit, wherein the working element holds the outer sheath and inner sheath in a position such that the distal end of the inner sheath is proximal to the inflow apertures for the outflow conduits and the outflow conduits merge with an outflow channel at a position proximal the inflow hole at the distal end of the inner sheath.

36. The endoscope of claim 35 wherein the tip element comprises a ceramic tip.

37. The endoscope of claim 36 wherein a portion of the outer sheath proximal the inflow at the distal end of the inner sheath contains a plurality of outflow holes directly communicating with the outflow channel.

38. The endoscope of claim 35 wherein the working element includes a portal for receiving an active cord for a throughput device.

* * * * *